United States Patent [19]

Bergman

[11] Patent Number: 5,477,327
[45] Date of Patent: Dec. 19, 1995

[54] HIGH RESOLUTION LOW NOISE OPTICAL POLARIMETER

[75] Inventor: John D. Bergman, Pittsburg, Calif.

[73] Assignee: Bergman Research Group, Inc., Pittsburg, Calif.

[21] Appl. No.: 168,119

[22] Filed: Dec. 15, 1993

[51] Int. Cl.$^6$ ............................... G01J 4/00; A61B 5/00
[52] U.S. Cl. ..................... 356/367; 356/368; 178/633; 178/664
[58] Field of Search .................... 356/364, 367, 356/368, 332, 333, 335; 128/633, 664

[56] References Cited

U.S. PATENT DOCUMENTS

| | | | |
|---|---|---|---|
| 3,612,689 | 10/1971 | Liskowitz | 356/364 |
| 3,958,560 | 5/1976 | March . | |
| 4,498,774 | 2/1985 | Yeung et al. | 356/368 |
| 4,819,752 | 4/1989 | Zelin | 128/633 |
| 4,863,265 | 9/1989 | Flower et al. | 128/633 |
| 4,901,728 | 2/1990 | Hutchinson | 356/368 |
| 5,009,230 | 4/1991 | Hutchinson | 356/368 |
| 5,168,326 | 12/1992 | Tokieda et al. | 356/368 |
| 5,183,042 | 2/1993 | Harjunmaa et al. | 128/633 |
| 5,209,231 | 5/1993 | Cote et al. | 356/367 |
| 5,243,983 | 9/1993 | Tarr et al. | 356/39 |

OTHER PUBLICATIONS

Gillham, E. J. et al. (1957) "A high-precision photoelectric polarimeter", *Journal of Scientific Instruments* 34:435–439.
Cote, Gerard L., et al. (1990) "Laser Polarimetry For Glucose Monitoring", *Annual International Conference of the IEEE Engineering in Medicine and Biology Society*, 12:476–477.
Cote, Gerard L., et al. (1990) "Optical Polarimetric Sensor For Blood Glucose Measurement", *IEEE*, 101–102.
Cote, Gerard L., et al, (1992) "Noninvasive Optical Polarimetric Glucose Sensing Using a True Phase Measurement Technique", *IEEE Transactions on Biomedical Engineering*, 39:752–756.
Rabinovitch, B. et al. (1982) "Noninvasive Glucose Monitoring of the Aqueous Humor of the Eye: Part I. Measurement of Very Small Optical Rotations", *Diaabaetes Care*, 5:254–258.
Müller, A. (undated) "In vivo Measurement of Glucose Concentration with Lasers", pp. 33–35.

Primary Examiner—Richard A. Rosenberger
Assistant Examiner—Jason D. Eisenberg
Attorney, Agent, or Firm—Townsend and Townsend and Crew

[57] ABSTRACT

Two linearly polarized beams of monochromatic laser light are amplitude modulated with low frequency sinusoids. The first laser is modulated with a sinusoid 90° out of phase from the second laser. The two beams of laser light have their polarization axis fixed and separated by 45°. These two beams are then collimated and combined into one composite beam using simple optics. This composite beam is then allowed to pass through an optically active substance of a calibrated path length. The laser radiation exiting the sample is passed through a optical notch pass filter, reducing any signal that may be present from any polarized ambient light by passing only light of the laser's frequency. The composite beam then passes into a beam splitting polarizing cube. This cube has the function of separating the beam into two orthogonal polarization components. The two beams of light exiting the cube are focused onto silicon photoelectric detectors. The cube is oriented such that one of the cube's transmission axis is aligned to coincide with the polarization axis of one of the lasers. The current from the detectors is converted into a voltage. The resulting detector voltages are then AC coupled to remove any DC component of the voltage, leaving only signal. These voltages are then subtracted using an instrumentation grade operational amplifier. The subtracted signal is phase shifted in direct proportion to solution concentration. Setting the ratio of laser signal amplitudes greater than unity can further amplify this phase shift to produce high instrument sensitivity.

22 Claims, 6 Drawing Sheets

HIGH RESOLUTION LOW NOISE OPTICAL POLARIMETER

A phase shifting optical polarimeter is composed of commonly available, inexpensive, compact parts and is completely solid state. The disclosed polarimeter uses a technique which is capable of accurately resolving very small, biologically significant, polarization vector rotations in the presence of large noise, such as the concentration of certain sugars in human blood.

BACKGROUND OF THE INVENTION

Glucose is an optically active substance. Its concentration in a given solution can be quantitatively measured using polarimetric techniques. The rotation of plane polarized light by an optically active substance is well known. The concentration of an optically active substance is related to the magnitude of the rotation observed, $\theta$, the wavelength of the light, $\lambda$, the material's thickness, D, specific rotation, $[\alpha]$, and its temperature, t.

$$\frac{\theta}{Dx[\alpha°]^{t,\lambda}} = \text{Concentration mg/dl} \quad (1)$$

If plane polarized light of incident intensity, $I_1$, is passed through a polarizing material (analyzer) having its transmission axis at some angle, $\alpha$, to the plane of the light's polarization, the transmitted intensity, $I_2$, is related to the square of the angle's cosine by Malus' law.

$$I_2 = I_1 \cos^2(\alpha) \quad (2)$$

Where $\alpha$ is the observed angle of rotation.

Human blood normally has a glucose concentration of between 80 and 120 mg/dl. The amount of polarization vector rotation imparted to plane polarized light with a wavelength of 670 nm by 100 mg of glucose dissolved in 1 dl of solution having a thickness of 1 cm and a temperature of 98.6° F. is on the order of 0.004°. Resolving rotation angles this small has become commonplace. However, in the presence of large noise, like that encountered in live human tissue, resolving angles of this magnitude becomes a formidable problem.

With an analyzer's transmission axis placed such that its parallel to the polarization axis of a beam of plane polarized monochromatic light which has a transparent optically active solution in its path, the intensity of light through the analyzer can be used to determine solution concentration, C. Combining equations 1 and 2:

$$\frac{1}{2D[\alpha]^{t,\lambda}} \times \cos^{-1}\left[\frac{2I_2 - I_1}{I_1}\right] = C \frac{mg}{dl} \quad (3)$$

Equation (3) is completely amplitude dependant and assumes that there is no absorption, scattering or other amplitude related noise. The device described herein employs the use of a phase shifting technique which is amplitude independent, eliminating the largest source of noise. Additionally, the unique optics arrangement facilitates a technique for linearly magnifying this phase shift, providing improved instrument sensitivity. I also employ the use of sophisticated electronics capable of recovering a very small signal from large noise.

SUMMARY OF THE INVENTION

Two linearly polarized beams of monochromatic laser light are amplitude modulated with low frequency sinusoids (for example less than 100 Hz). The first laser is modulated with a sinusoid 90° out of phase from the second laser. These two beams are then collimated and combined into one composite beam using simple optics. This composite beam is then allowed to pass through an optically active substance of a calibrated path length. The laser radiation exiting the sample is passed through a optical notch pass filter, reducing any signal that may be present from any polarized ambient light by passing only light of the laser's frequency. The composite beam then passes into a beam splitting polarizing cube. This cube has the function of separating the beam into two orthogonal polarization components. The two beams of light exiting the cube are focused onto silicon photoelectric detectors. The cube is oriented such that one of the cube's transmission axis is aligned to coincide with the polarization axis of one of the lasers. The current from the detectors is converted into a voltage. The resulting detector voltages are then AC coupled to remove any DC component of the voltage, leaving only signal. These voltages are then subtracted using an instrumentation grade operational amplifier. This subtraction removes any component of signal resulting from common mode electrical noise, randomly polarized light, or scattering in the sample. The subtracted signal is phase shifted in direct proportion to solution concentration. The phase shift is measured and the solution concentration calculated. Setting the ratio of laser signal amplitudes greater than unity can further amplify this phase shift to produce high instrument sensitivity.

BRIEF DESCRIPTION OF THE DRAWINGS

Other objects, features and advantages of this invention will be more apparent after referring to the following specification and attached drawings in which.

DESCRIPTION OF THE PREFERRED EMBODIMENT

Figure 1:
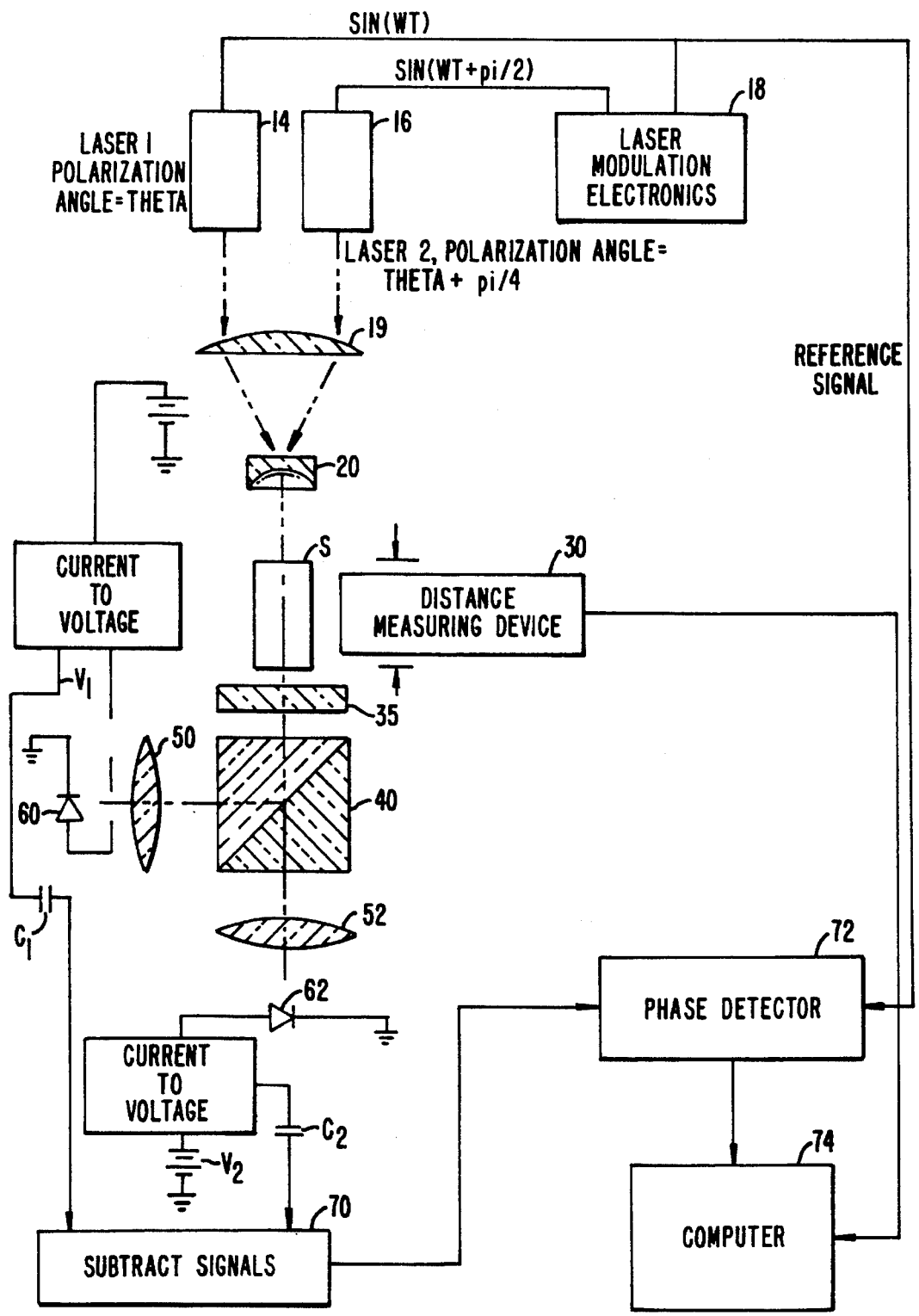
FIGS. 1 is a schematic of the instrument of this invention.
Figure 2A:
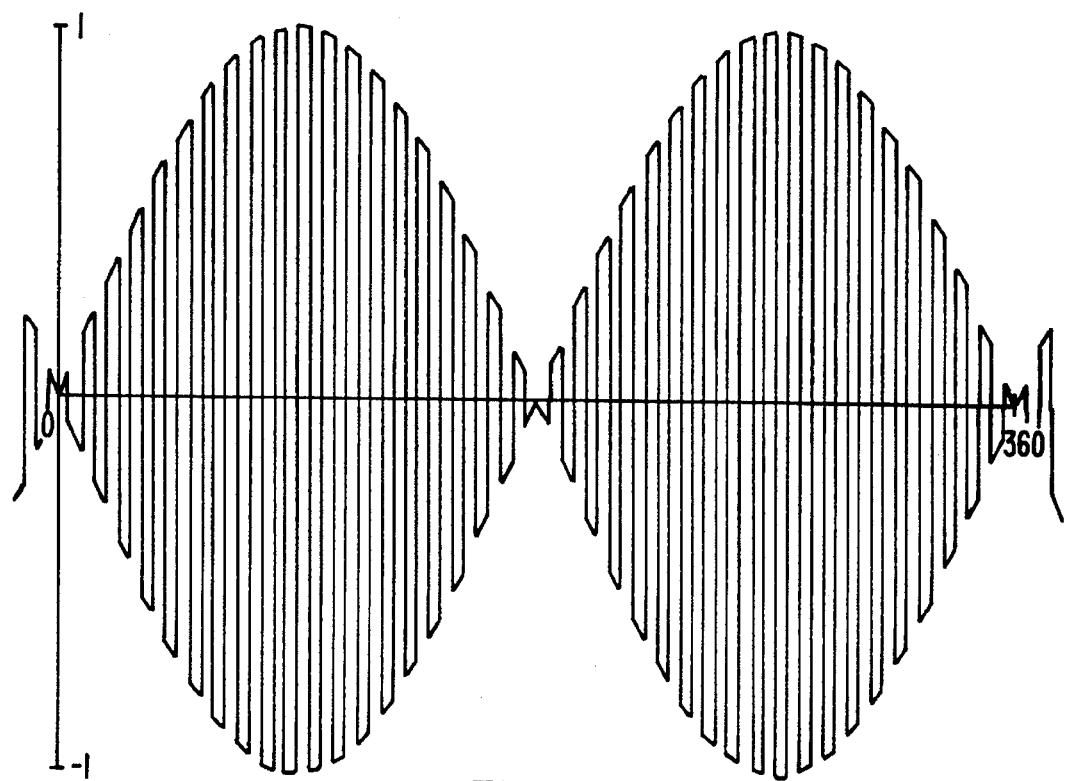
FIG. 2A and 2B are phase diagrams of the modulated laser output.
Figure 2B:
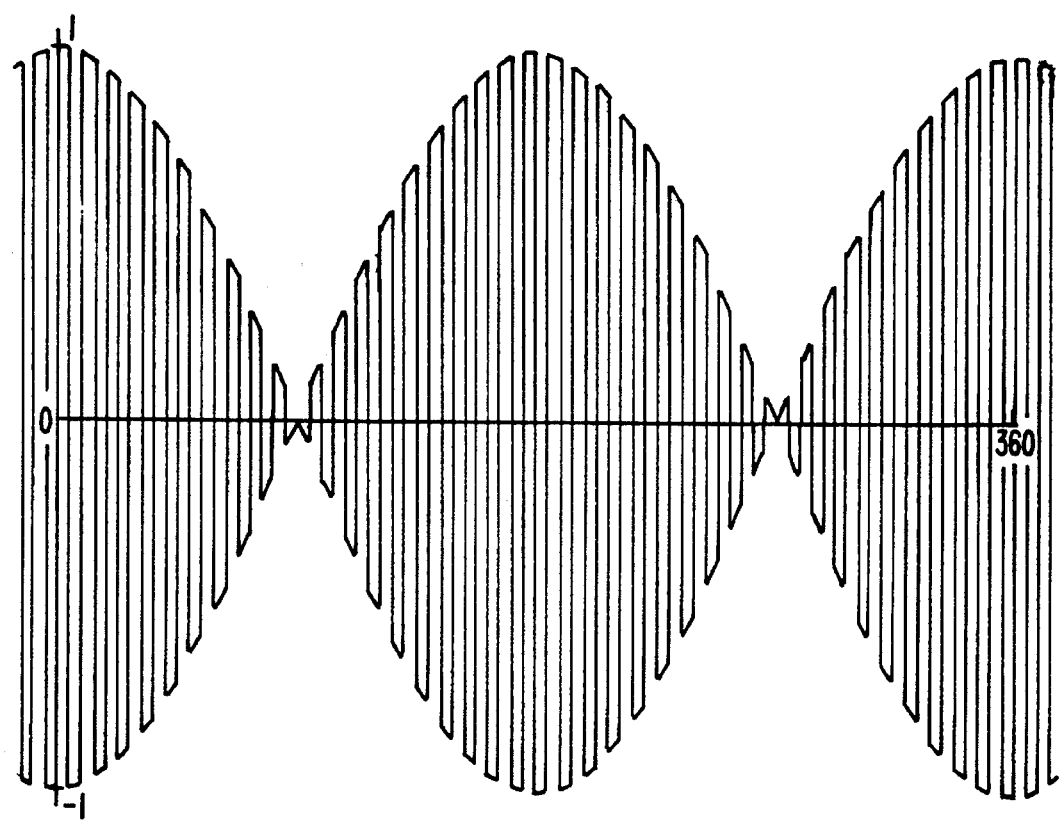
Figure 3A:
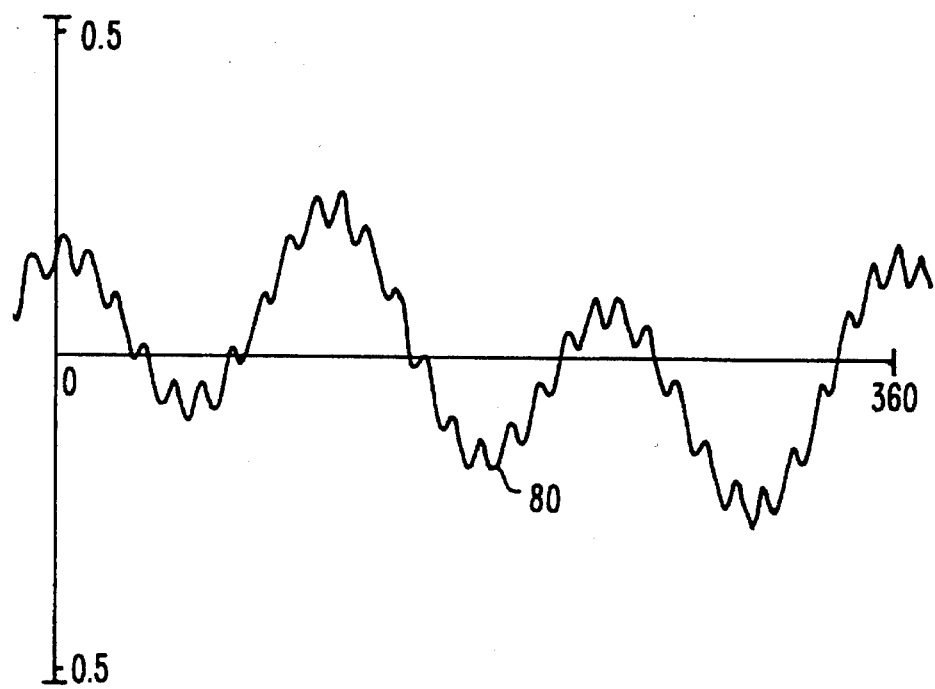
FIGS. 3A, 3B, 3C and 3D are respective plots of a composite of the detected waveform showing noise, the modulated signal with the noise added, the demodulated wave form with symmetric noise ready to be filtered, and finally the filtered output signal.
Figure 3B:
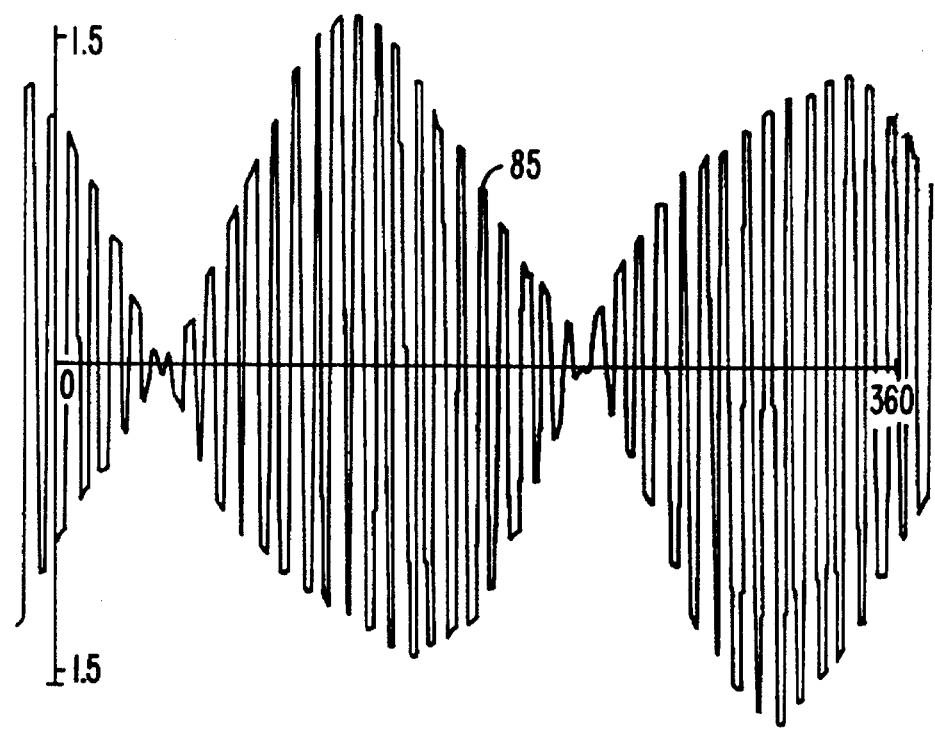
Figure 3C:
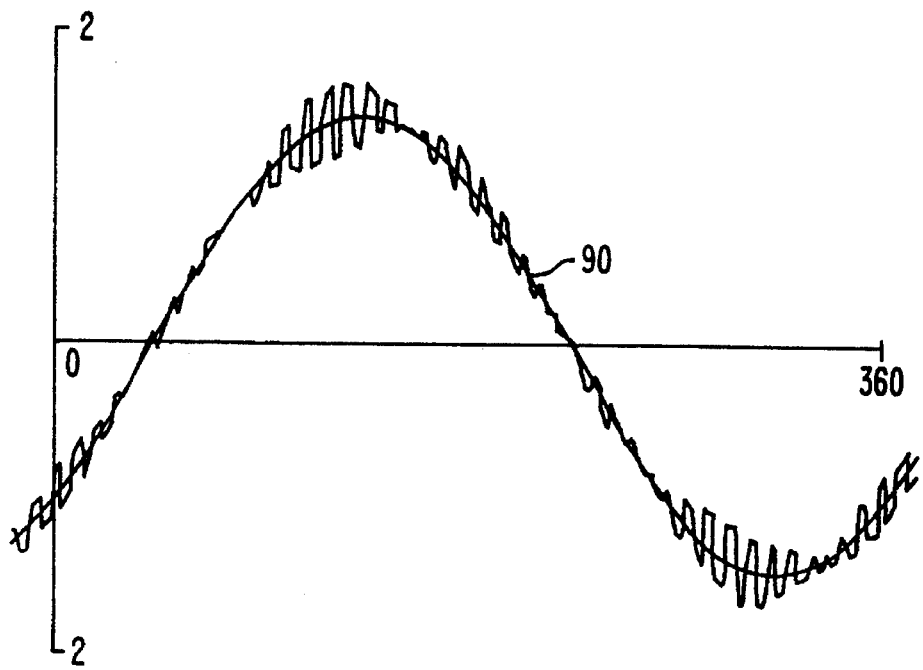
Figure 3D:
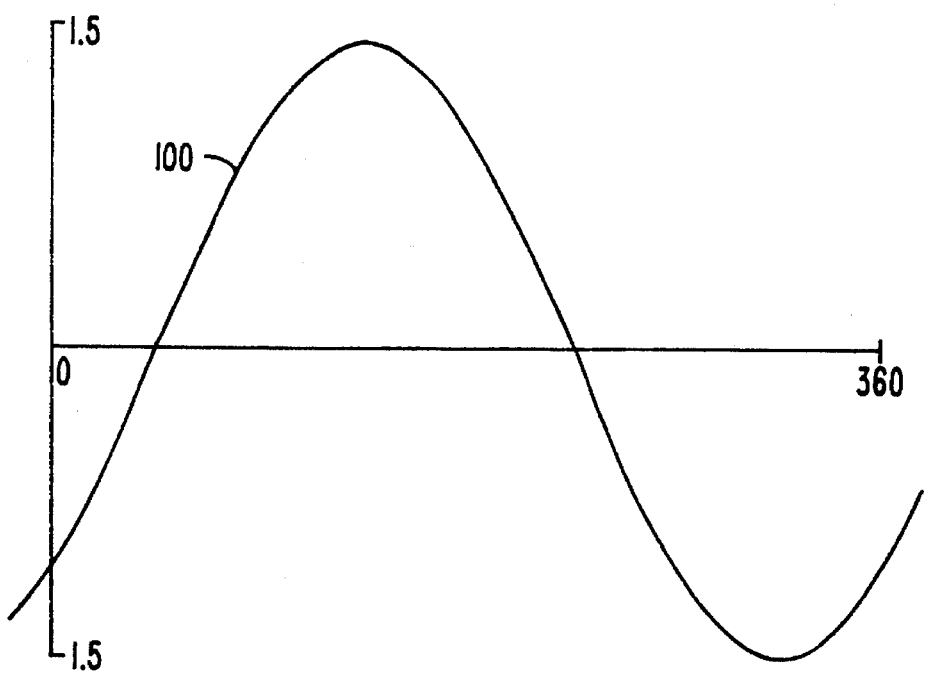

Referring to FIG. 1, two lasers 14, 16 driven by conventional modulating electronics 18 emit linearly polarized beams of monochromatic laser light. These lasers 14, 16 are amplitude modulated with low frequency sinusoids. (See FIGS. 2A and 2B). The first laser 14 is modulated with a sinusoid 90° out of phase from second laser 16.

The signal on laser 14 will be denominated as a sine wave; the signal on laser 16 will be denominated a cosine wave. Laser 16 has its polarization vector set such that it is rotated 45° from the polarization vector of laser 14. The polarization vectors of the two lasers are thus fixed and do not change. The only time variant quality of the light exiting the lasers are their amplitude modulation.

Signal impressed upon the carrier wave modulating laser 14 can be mathematically set forth:

$A_1 \sin(\omega t)$, Plane polarized at angle $\theta$

Signal impressed upon the carrier wave modulating laser 16 can be expressed:

$A_2 \cos(\omega t)$, Plane polarized at angle $\theta + 45°$

Where $A_1$ and $A_2$ are signal amplitudes and $\theta$ is an arbitrary reference to describe the laser's plane of polarization.

These two beams are then collimated and combined into one composite beam using simple optics including plano-convex lens 19 and plano-concave lens 20. This composite beam is then allowed to pass through an optically active sample of a calibrated path length measured at distance device 30. This has the function of rotating the polarization vectors of the composite beam in direct proportion to the concentration of optically active constituent present.

The laser radiation exiting the sample is passed through a optical notch pass filter 35, reducing any signal that may be present from any polarized ambient light by passing only light of the laser's frequency. The composite beam then passes into a beam splitting polarizing cube 40. This cube has the function of separating the beam into two orthogonal polarization components.

The two beams of light exiting the cube 40 are focused by respective lenses 50, 52 onto silicon photoelectric detectors 60, 62. The cube 40 is oriented such that one of the cube's transmission axis is aligned to coincide with the polarization axis of laser 14.

Presuming the absence of sample S, all of the light from laser 14 will pass through the cube 40 to impinge upon detector 60. It follows that the light from laser 16, with its polarization vector set 45° from the first, will be split in half and impinge equally upon both detectors. The current produced by the incident light on the detectors is directly related to the light's intensity. The current from the detectors is converted into a voltage $V_1$, $V_2$. The resulting detector voltages are then AC at capacitors $C_1$, $C_2$ coupled to remove any DC component of the voltage, leaving only signal.

Presuming that a sample S is present causing rotation: From equation (2): Detector 62 demodulated and filtered signal:

$$\cos^2(\alpha)[A_1 \sin(\omega t)] + \cos^2(45° + \alpha)[A_2 \cos(\omega t)] \quad (4)$$

Detector 60 demodulated and filtered signal:

$$\sin^2(-\alpha)[A_1 \sin(\omega t)] + \cos^2(45° - \alpha)[A_2 \cos(\omega t)] \quad (5)$$

Where $\alpha$ is the rotation of polarization vectors.

These voltages are then subtracted using an instrumentation grade operational amplifier 70. This subtraction removes any component of signal resulting from common mode electrical noise, randomly polarized light, or scattering in the sample S. Detector 62—Detector 60 demodulated and filtered signals:

$$A_1 \sin(\omega t)[\cos^2(\alpha) - \sin^2(-\alpha)] - A_2 \cos(\omega t)[\cos^2(45° + \alpha) - \cos^2(45° - \alpha)]$$

Scattering in the sample would produce a component of signal which is randomly polarized and thus equally distributed to the detectors. Therefore, when the signals from the detectors are subtracted, only the signal due to the fraction of light retaining its original polarization, though perhaps rotated, remains.

With no sample S in the path of the composite beam, the resultant subtracted signal is in phase with the signal on laser #1 ($\sin(\omega t)$). However, placing an optically active substance in the path of the composite beam imparts a rotation of polarization vectors. Now, with this polarization rotation, subtracting the detector voltages yields a resultant sinusoid wave form that is phase shifted from the signal on laser 14.

Referring to FIGS. 3A–3D, the signal produced by this invention can be viewed at various stages of the signal processing. Noise is schematically set forth in the form of sinusoids at 80 in FIG. 3A. Signal plus noise is shown at 85 in FIG. 3B. A demodulated wave form with symmetric noise, ready to be filtered is shown at 90 in FIG. 3C. Finally, the recovered demodulated and filtered wave form is shown at 100 in FIG. 3D. The reader will understand that wave form phase analysis can occur through a phase detector 72 and computer 74.

Figure 4:
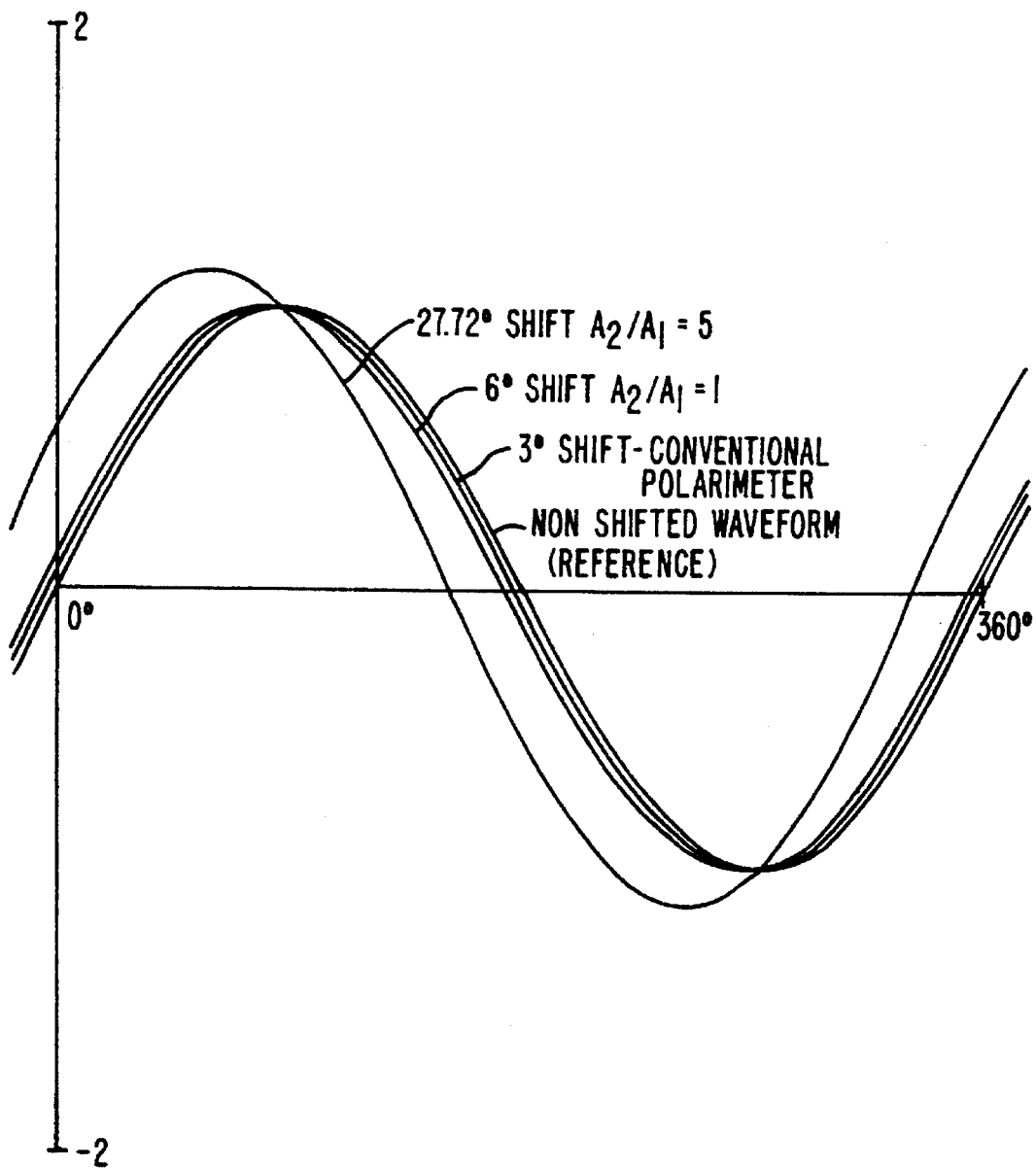
FIG. 4 is a plot of a sample having three degrees of rotation (3°) illustrating the increased phase shift possible by the amplitude ratio of the laser signals being greater than or equal to unity; and, FIG. 5 is a plot of degrees of polarization rotation versus observed instrument waveform phase shifting for the differentially amplified detector signals resulting in increased instrument sensitivity.

Referring to FIG. 4 with a laser signal amplitude ratio ($A_2/A_1$) of unity, the shift in phase will be equal to twice the angular rotation of the polarization vectors. This phase shift magnification is a consequence of this polarimeter's design and aids in its sensitivity. Setting the ratio of laser signal amplitudes greater than unity, typically $A_2/A_1 = 5$, can further magnify this phase shift. In the example here, what would be a phase shift on the order of 3° observed in a conventional polarimeter, can be a phase shift in the order of 27.72° for $A_2/A_1 = 5$. Thus, for low concentrations of optically active material in the path of the polarimeter, greater sensitivity is achieved.

Figure 5:
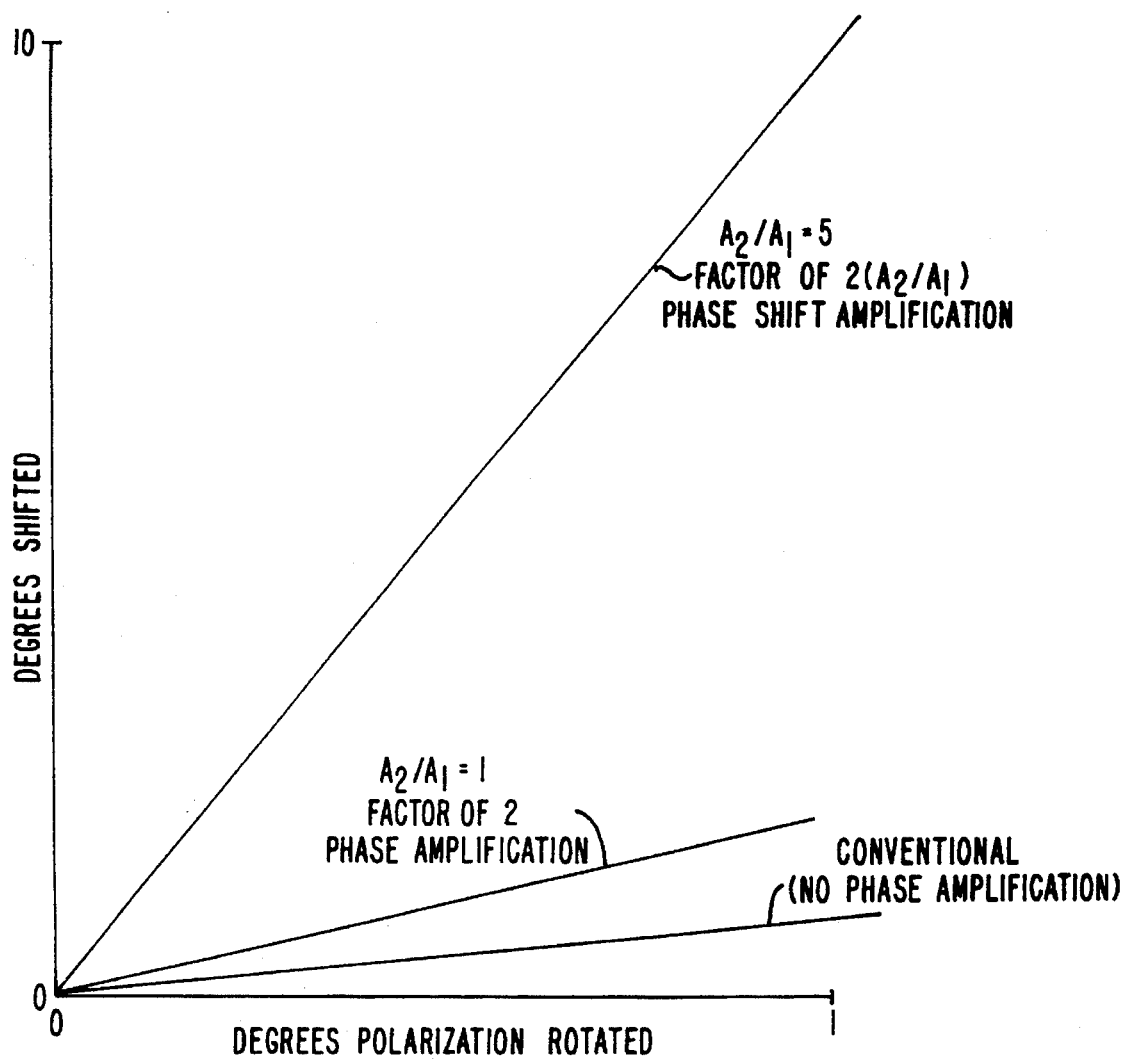

For small polarization rotations, the total phase shift amplification produced by these techniques can be approximated to be linear and equal to $2(A_2/A_1)$. (See FIG. 5) For example, using a conventional phase shifting polarimeter, a polarization rotation of 4.5 milli-degrees would result in a signal phase shift of 4.5 milli-degrees, an expected rotation for the glucose concentration present in human blood using a path length of 1 cm. The polarimeter described in this paper, with its phase amplification techniques, will exhibit a signal phase shift of about 45 milli-degrees (e.g. 10 times 4.5 milli-degrees).

The function yielding the magnitude of signal phase shift for a given positive rotation:

$$\phi = -\tan^{-1}\left[\frac{A_2}{A_1} \times \frac{\cos^2(45° + \alpha) - \cos^2(45° - \alpha)}{\cos^2(\alpha) - \sin^2(-\alpha)}\right] \quad (7)$$

Where $\phi$ = observed signal phase shift and $\alpha$ is the polarization rotation of the composite beam.

It will be understood that the present invention has been illustrated with respect to the measurement of sugar, preferably in human blood. The reader will understand that this disclosure is applicable to polarimeter utilized in other fields.

I have used the term "linearly" polarized. This will be understood to include so-called "elliptical polarization" in which linear polarization along one axis significantly exceeds polarization along the remaining axis.

What is claimed is:

1. A polarimeter comprising in combination:

first and second means for emitting respective first and second amplitude modulated linearly polarized beams of monochromatic light having a polarization axis, said first amplitude modulated linearly polarized beam of monochromatic light with said polarization axis non-collinear with said polarization axis of said second amplitude modulated linearly polarized beam of monochromatic light, said amplitude modulation including imposition of a sinusoid on both said beams, said first amplitude modulated linearly polarized beam of monochromatic light modulated with said imposed sinusoid out of phase from said imposed sinusoid on said second amplitude modulated linearly polarized beam of monochromatic light;

an optical path including a transparent, optically active sample of known length in said optical path;

means for combining said first and second amplitude modulated linearly polarized beams of monochromatic light and emitting said combined beam into said optical path;

means for separating said combined beam into two orthoganal polarization components in said optical path;

first and second photoelectric detectors for detecting said two orthoganal polarization components and emitting respective signals proportional to said components;

means for subtracting said respective signals from said first and second photoelectric detectors for removing common mode noise and obtaining a received amplitude modulated sinusoid; and, means for comparing phase of said received amplitude modulated sinusoid with phase of said imposed sinusoids on respective first and second amplitude modulated linearly polarized beams of monochromatic light obtaining a phase difference proportional to polarization rotation within said sample.

2. A polarimeter according to claim 1 and further wherein:

said means for separating said combined beam into said two orthogonal polarization components includes a beam splitting polarizing cube having a transmission axis.

3. A polarimeter according to claim 2 and further wherein:

said means for combining said first and second amplitude modulated linearly polarized beams of monochromatic light includes simple optics having spherical lenses.

4. A polarimeter according to claim 2 and further wherein:

said beam splitting polarizing cube is oriented with respect to said first and second amplitude modulated linearly polarized beams of monochromatic light such that said beam splitting polarizing cube having a transmission axis is aligned to coincide with said polarization axis of one of said amplitude modulated linearly polarized monochromatic light beams.

5. A polarimeter according to claim 1 and further wherein:

said first amplitude modulated linearly polarized beam of monochromatic light has said polarization axis offset 45° from said polarization axis of said second amplitude modulated linearly polarized beam of monochromatic light.

6. A polarimeter according to claim 1 and further wherein:

means modulating said first and second amplitude modulated linearly polarized beams of monochromatic light include said imposed sinusoids of a frequency less than 100 Hz.

7. A polarimeter according to claim 1 and further including:

an optical notch filter in said optical path between said transparent, optically active sample and said photoelectric detectors for passing light only of said monochromatic light.

8. A polarimeter according to claim 1 and further including:

means for converting said respective signals from said first and second photoelectric detectors to electrical voltages.

9. A polarimeter according to claim 8 and further wherein:

said resulting detector voltages are AC coupled to remove any DC component of said voltage.

10. A polarimeter according to claim 1 and further wherein:

said means for subtracting said signals from said first and second photoelectric detectors constitutes an instrumentation grade operational amplifier.

11. A polarimeter according to claim 1 and further including:

means for setting an amplitude ratio of said imposed sinusoids on said first and second amplitude modulated linearly polarized beams of monochromatic light greater than unity whereby said means for comparing further amplifies said phase difference to produce high instrument sensitivity.

12. A process for polarimetry comprising the steps of:

emitting respective first and second amplitude modulated linearly polarized beams of monochromatic light having a polarization axis, said first amplitude modulated linearly polarized beam of monochromatic light having said polarization axis non-collinear with said polarization axis of said second amplitude modulated linearly polarized beam of monochromatic light, said amplitude modulation including imposition of a sinusoid on both said beams; said first amplitude modulated linearly polarized beam of monochromatic light modulated with said imposed sinusoid out of phase from said imposed sinusoid on said second amplitude modulated linearly polarized beam of monochromatic light;

combining said first and second amplitude modulated linearly polarized beams of monochromatic light;

emitting said combined beam into an optical path including a transparent optically active sample of known length in said optical path;

placing means for separating said combined beam into two orthoganal polarization components in said optical path;

providing first and second photoelectric detectors for detecting said two orthoganal polarization components and emitting a signal proportional to said components;

subtracting said signals from said first and second photoelectric detectors for removing common mode noise and obtaining a received amplitude modulated sinusoid; and, comparing phase of said received amplitude modulated sinusoid with phase of said imposed sinusoids on said respective first and second amplitude modulated linearly polarized beams of monochromatic light obtaining a phase difference proportional to polarization rotation within said sample.

13. A process for polarimetry according to claim 12 including the further steps of:

setting an amplitude ratio of said imposed sinusoids on said first and second amplitude modulated linearly polarized beams of monochromatic light greater than unity whereby said process further amplifies said phase difference to produce high instrument sensitivity.

14. A process for polarimetry according to claim 12 and including the further steps of:

emitting said first amplitude modulated linearly polarized beam of monochromatic light with said polarization axis offset 45° from said polarization axis of said second amplitude modulated linearly polarized beam of monochromatic light.

15. A process for polarimetry according to claim 12 including the further steps of:

modulating said first and second amplitude modulated linearly polarized beams of monochromatic light with said imposed sinusoids that are 90° out of phase.

16. A process for polarimetry according to claim 15 including the further steps of:

modulating said first and second amplitude modulated linearly polarized beams of monochromatic light with said imposed sinusoids of a frequency less than 100 Hz.

17. A process for polarimetry according to claim 12 and further wherein:

said combining said first and second amplitude modulated linearly polarized beams of monochromatic light constitutes providing simple optics having spherical lenses; and, routing said beams through said simple optics.

18. A process for polarimetry according to claim 12 including the further steps of:

providing an optical notch filter between said sample and said photoelectric detectors for passing light only of said monochromatic light.

19. A process for polarimetry according to claim 12 and further wherein:

said separating said combined beam constitutes orienting a beam splitting polarizing cube with respect to said first and second light beams such that said beam splitting polarizing cube has a transmission axis aligned to coincide with said polarization axis of one of said first and second amplitude modulated linearly polarized beams of monochromatic light; and routing said beams through said beam splitting polarizing cube.

20. A process for polarimetry according to claim 12 including the further steps of:

converting said signal from said first photoelectric detectors to electrical voltages.

21. A process for polarimetry according to claim 20 including the further steps of:

AC coupling said signal from said first and second photoelectric detectors to remove any DC component of said voltage.

22. A process for polarimetry according to claim 12 and further wherein:

said subtracting said signals from said first and second photoelectric detectors constitutes providing an instrumentation grade operational amplifier; and, routing said signals through said instrumentation grade operational amplifier.

\* \* \* \* \*